(12) United States Patent
Butts et al.

(10) Patent No.: US 6,312,433 B1
(45) Date of Patent: Nov. 6, 2001

(54) DEFORMABLE INTRAOCULAR LENS INJECTING APPARATUS AND METHOD

(75) Inventors: Maurice D. Butts, Fullerton; Thomas J. Chambers, Upland, both of CA (US)

(73) Assignee: STAAR Surgical Company, Inc., Monrovia, CA (US)

(*) Notice: Subject to any disclaimer, the term of this patent is extended or adjusted under 35 U.S.C. 154(b) by 0 days.

(21) Appl. No.: 09/422,984

(22) Filed: Oct. 22, 1999

(51) Int. Cl.$^7$ .................................................. A61F 9/00
(52) U.S. Cl. ............................................................. 606/107
(58) Field of Search ........................ 606/107; 623/6.12, 623/907; 604/220

(56) References Cited

U.S. PATENT DOCUMENTS

| | | | |
|---|---|---|---|
| 2,224,575 | * 12/1940 | Montalvo-Guenard | 606/107 |
| 4,681,102 | * 7/1987 | Bartell | 623/6.12 |
| 4,834,094 | * 5/1989 | Patton et al. | 606/107 |
| 5,222,945 | * 6/1993 | Basmight | 604/220 |
| 5,499,987 | * 3/1996 | Feingold | 606/107 |
| 5,582,614 | * 12/1996 | Feingold | 606/107 |
| 5,616,148 | * 4/1997 | Eagles et al. | 606/107 |
| 5,643,276 | * 7/1997 | Zaleski | 606/107 |
| 5,702,402 | * 12/1997 | Brady | 606/107 |
| 5,803,925 | * 9/1998 | Yang et al. | 606/107 |
| 5,873,879 | * 2/1999 | Figueroa et al. | 606/107 |
| 5,947,975 | * 9/1999 | Kikuchi et al. | 606/107 |

* cited by examiner

*Primary Examiner*—Jeffrey A. Smith
*Assistant Examiner*—Eduardo C. Robert
(74) *Attorney, Agent, or Firm*—William L. Klima; Law Offices of William L. Klima, P.C.

(57) ABSTRACT

A deformable intraocular lens injecting apparatus for inserting a deformable intraocular lens through a small incision into an eye. The lens injecting apparatus includes a lens injecting body including a lens receiver configured to be operated between an open configuration and a closed configuration and a nozzle portion provided with a tip portion configured to be inserted through a small incision into an eye. The nozzle portion is configured for connection to the lens injecting body and the nozzle portion and the lens receiver define a lens delivery passageway.

30 Claims, 5 Drawing Sheets

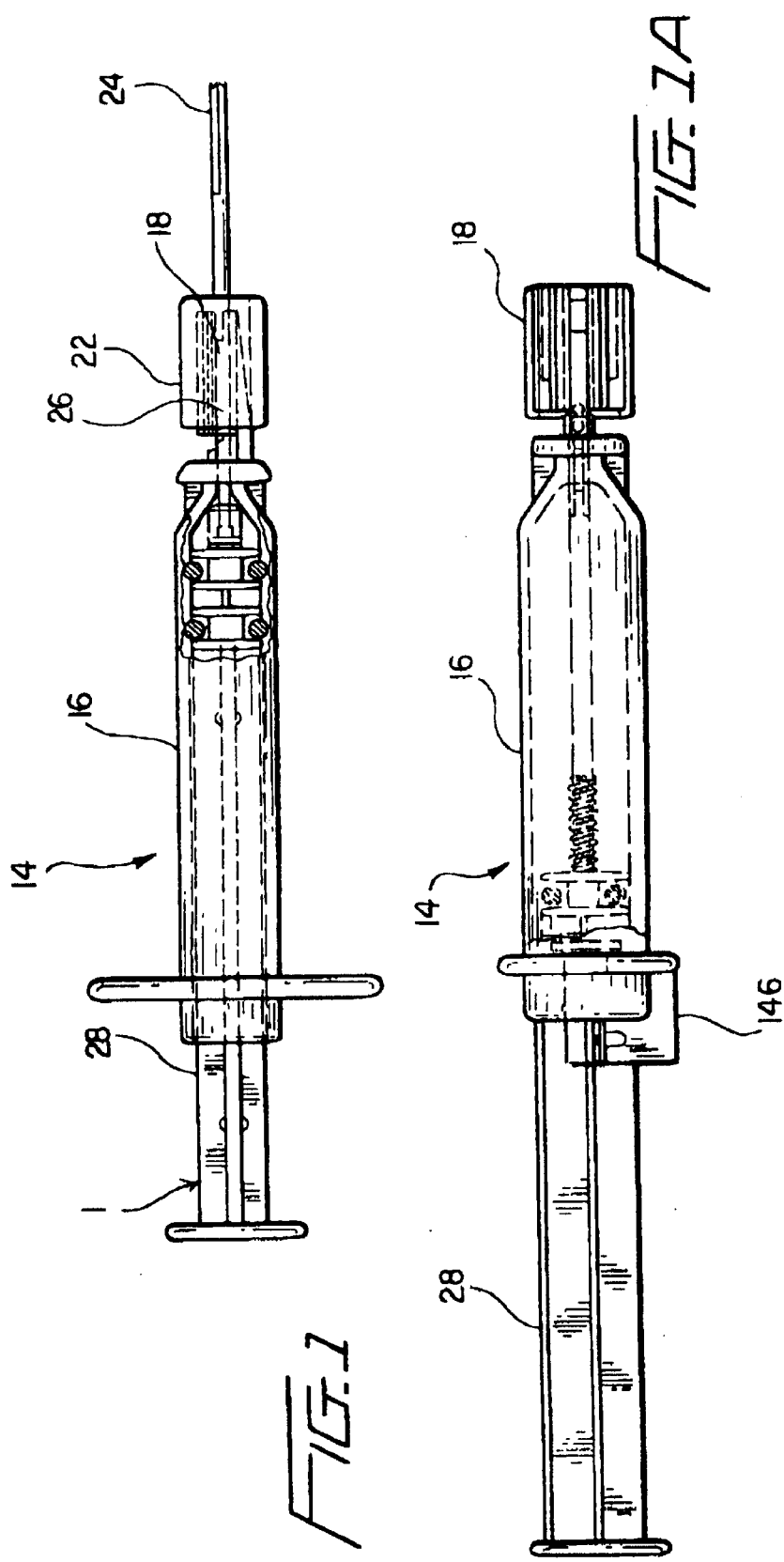

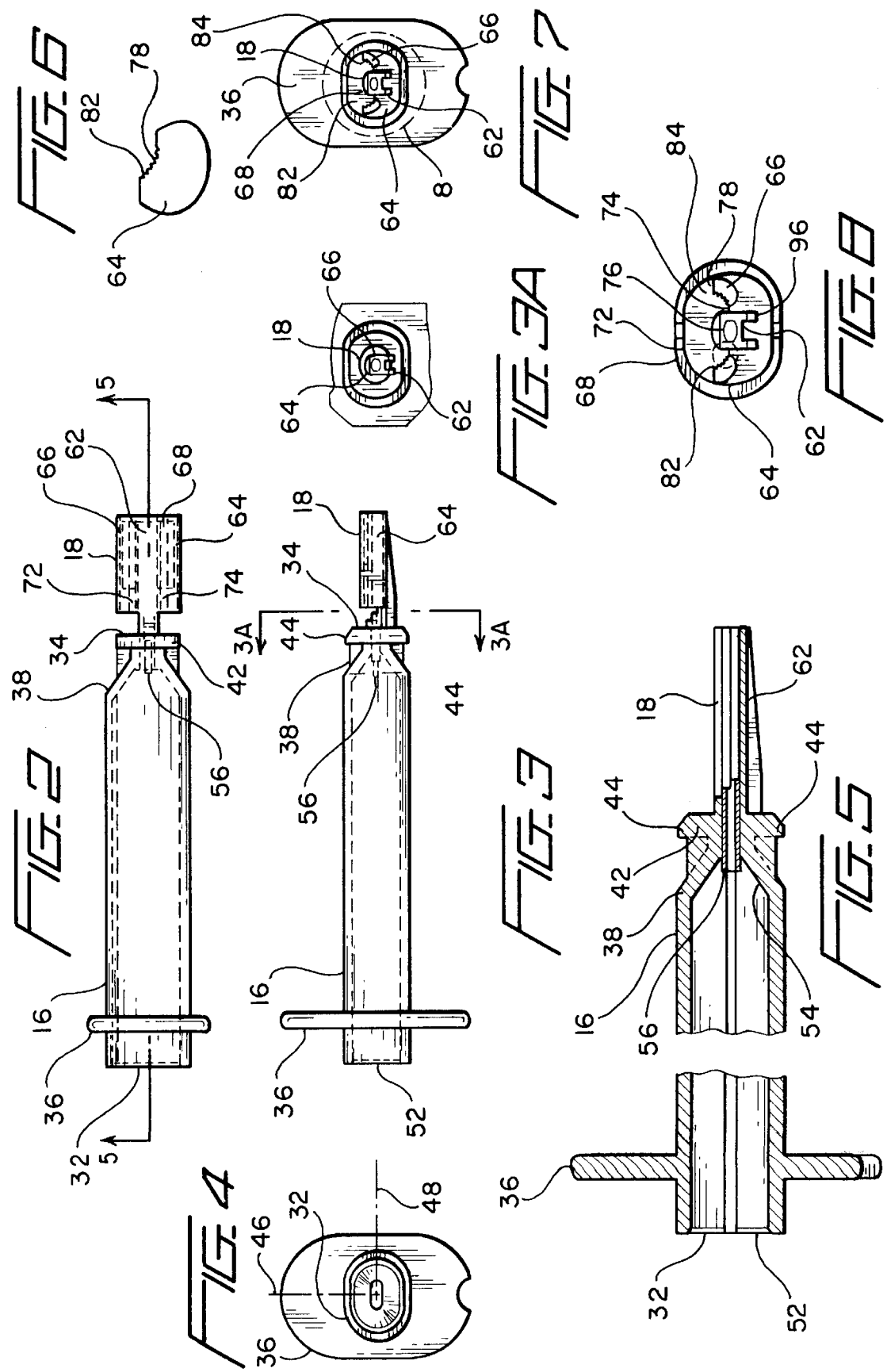

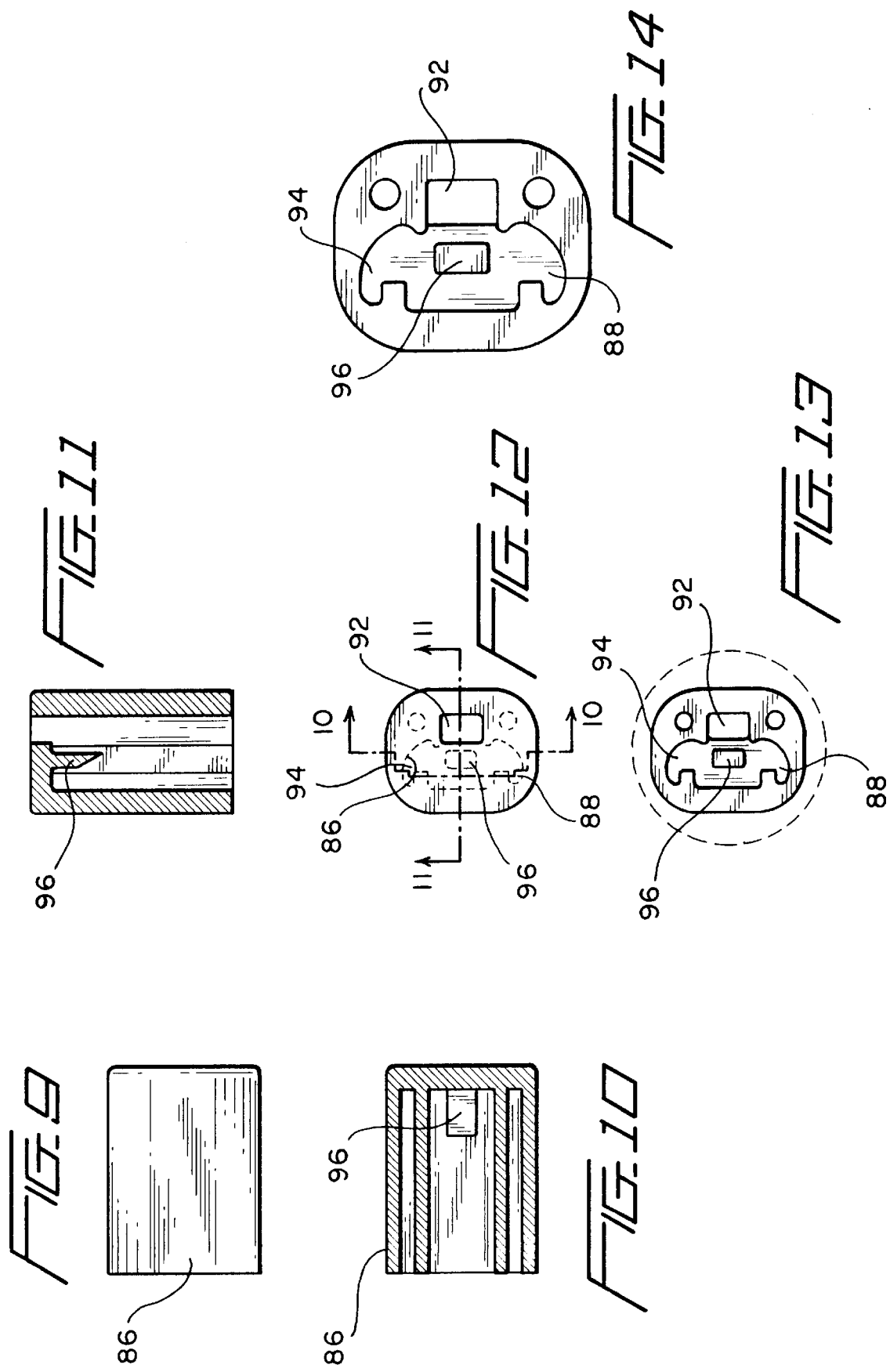

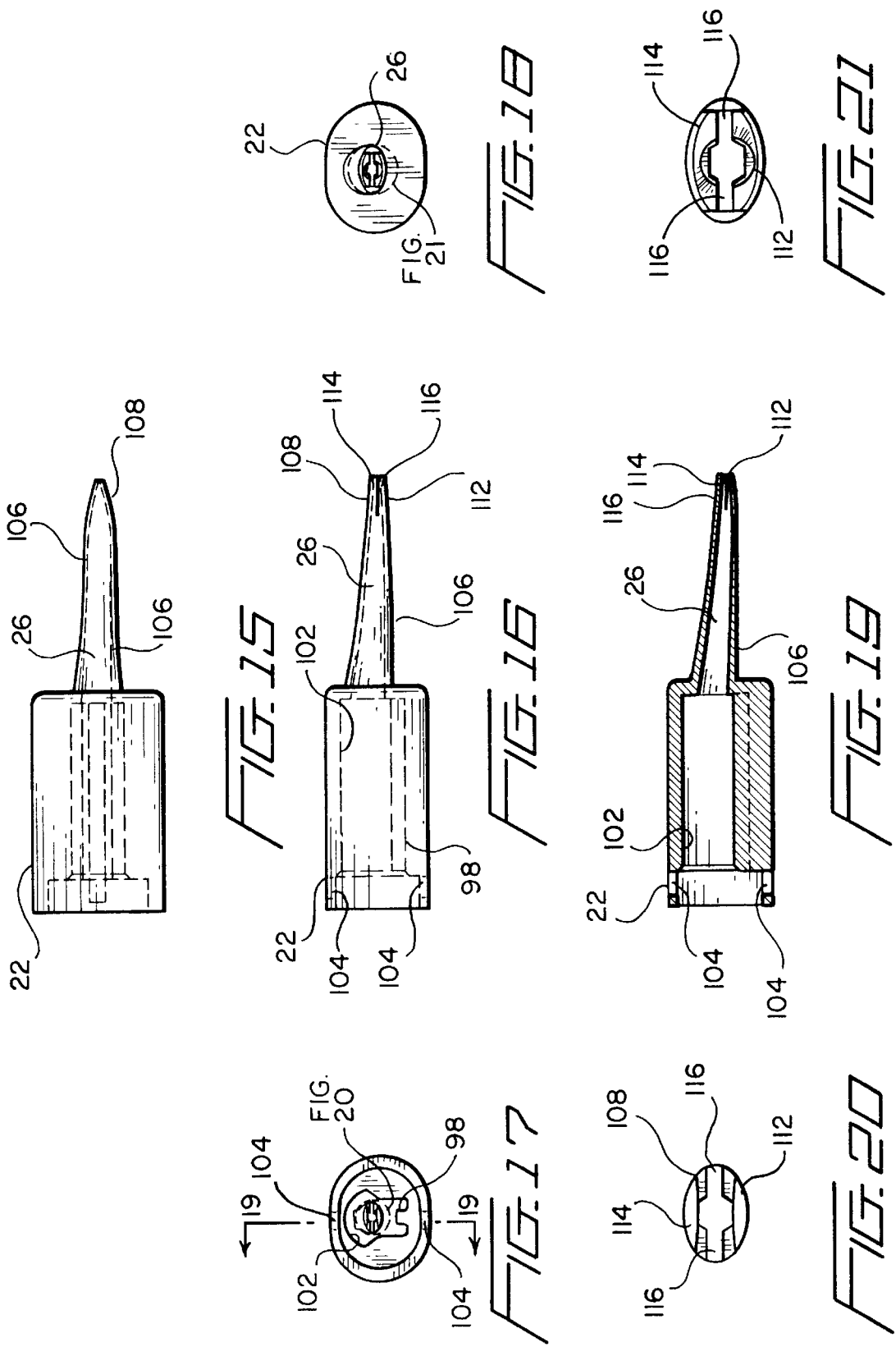

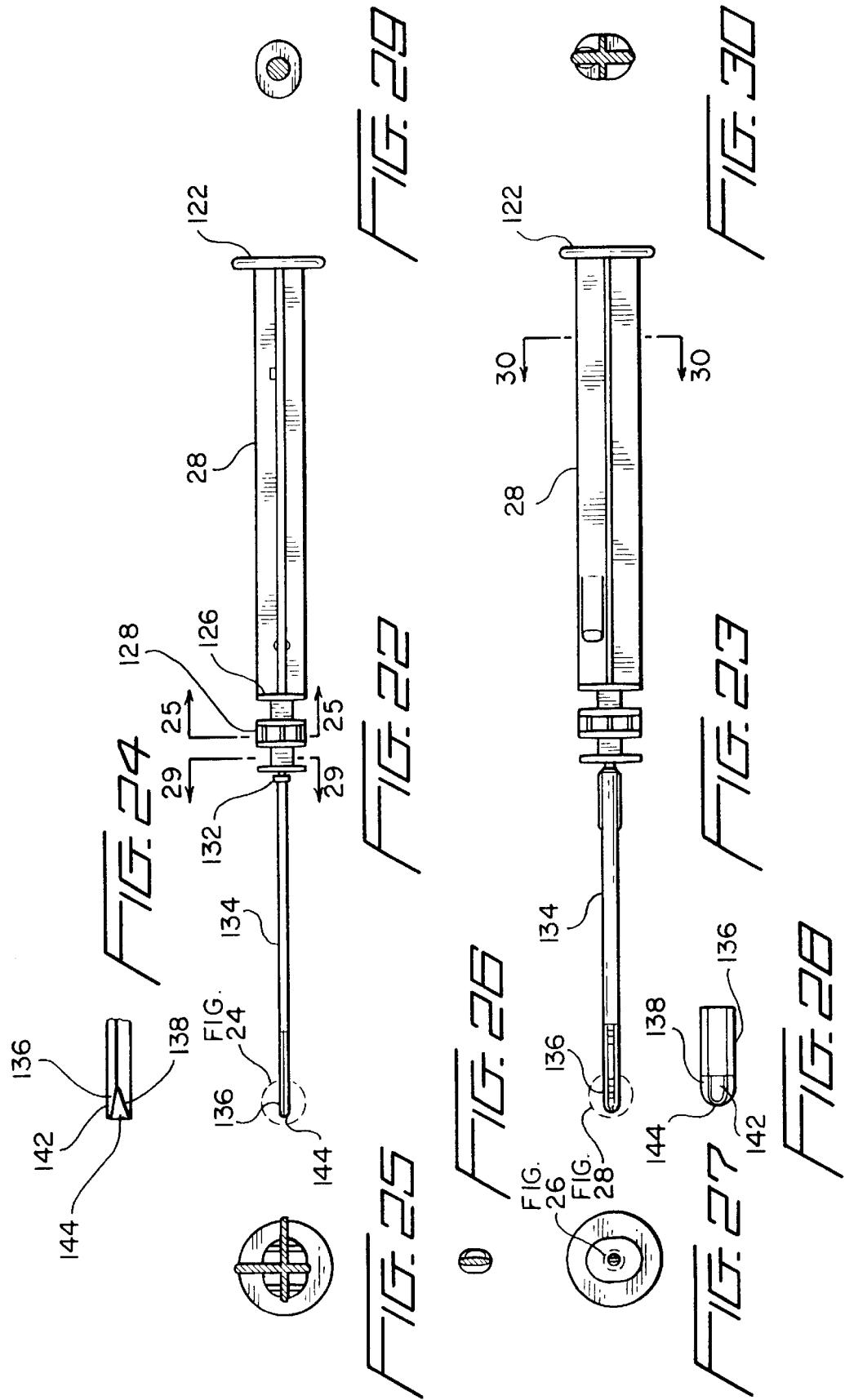

US 6,312,433 B1

DEFORMABLE INTRAOCULAR LENS INJECTING APPARATUS AND METHOD

FIELD OF THE INVENTION

The present invention relates to the introduction of an artificial lens to an eye. More specifically, the present invention relates to an apparatus and method for implanting a deformable intraocular lens into an eye.

BACKGROUND OF THE INVENTION

The use of deformable intraocular lenses in the treatment of cataracts and other refractive problems has become commonplace. There are many devices and methods currently in use for the delivery of a deformable intraocular lens into the eye. Complications continue to arise out of the use of these devices and methods, specifically, damage to the ocular tissues and/or damage to the implanted deformable intraocular lens. There is a need for an apparatus and method for delivering a deformable intraocular lens to the eye which does not damage the ocular tissue or the implanted lens.

SUMMARY OF THE INVENTION

It is a first object of the present invention to provide an apparatus and method for introducing a deformable intraocular lens to the eye.

It is a second object of the present invention to provide an improved apparatus and method for introducing a deformable intraocular lens to the eye.

It is a third object of the present invention to provide an apparatus which deforms a deformable intraocular lens for introduction through a small ocular incision to the eye.

It is a fourth object of the present invention to provide an apparatus which moves a deformed intraocular lens into the eye.

It is a fifth object of the present invention to provide an apparatus which allows a deformed intraocular lens to release stored energy associated with the lens deformation process in a controlled manner.

It is a sixth object of the present invention to provide an apparatus which provides at least one tool for manipulating a lens within the eye.

It is a seventh object of the present invention to provide an apparatus which may be pre-loaded with a deformable intraocular lens.

It is an eighth object of the present invention to provide an apparatus which may be pre-loaded with a deformable intraocular lens in a non-deformed condition.

It is a ninth object of the present invention to reduce the potential for introduction of user error into the process for the delivery of a deformable intraocular lens to the eye.

It is a tenth object of the present invention to further automate the process for delivering a deformable intraocular lens to the eye.

It is an eleventh object of the present invention to provide an apparatus which allows a surgeon to view a deformed intraocular lens for determining whether the deformation of the lens is correct for delivery of the lens to the eye.

It is a twelfth object of the present invention to provide an apparatus which allows a surgeon to deform a deformable intraocular lens in preparation for delivery of the lens to the eye without the use of forceps.

It is a thirteenth object of the present invention to provide a deformable intraocular lens injecting apparatus including a lens injecting body including a lens receiver configured to be operated between an open configuration and a closed configuration, a nozzle portion provided with a tip portion configured to be inserted through a small incision into an eye, the nozzle portion configured for connection to the lens receiver of the lens injecting body, the nozzle portion and the lens receiver defining a lens delivery passageway, and a plunger slidably disposed relative to the lens delivery passageway and configured to engage a deformable intraocular lens within the lens delivery passageway of the lens receiver and to move the deformable intraocular lens out of the lens delivery passageway into the eye.

The present invention provides an apparatus and method for inserting a deformable intraocular lens through a small incision into an eye. In a preferred embodiment the apparatus includes a lens injecting body including a lens receiver configured to be operated between an open configuration and a closed configuration, a nozzle portion provided with a tip portion configured to be inserted through a small incision into an eye, the nozzle portion configured for connection to the lens receiver of the lens injecting body, the nozzle portion and the lens receiver defining a lens delivery passageway; and, a plunger slidably disposed relative to the lens delivery passageway and configured to engage a deformable intraocular lens within the lens delivery passageway of the lens receiver, and to move the deformable intraocular lens out of the lens delivery passageway into the eye.

The apparatus of the present invention stores, deforms, and delivers a deformable intraocular lens to the eye.

BRIEF DESCRIPTION OF THE DRAWINGS

FIG. 1 shows a side view of an apparatus according to the present invention.

FIG. 1A shows another side view of an apparatus according to the present invention.

FIG. 2 shows a planar view of a lens injecting body according to the present invention.

FIG. 3 shows a side view of the lens injecting body shown in FIG. 2.

FIG. 3A shows an end view of the lens injecting body shown in FIG. 2

FIG. 4 shows an end view of the lens injecting body shown in FIG. 2.

FIG. 5 shows a partially exploded view of the lens injecting body shown in FIG. 2

FIG. 6 shows an end view of an extension portion according to the present invention.

FIG. 7 shows an end view of a lens receiver according to the present invention.

FIG. 8 shows an end view of a lens receiver according to the present invention.

FIG. 9 shows a side view of a cap according to the present invention.

FIG. 10 shows a cross-sectional view of the cap shown in FIG. 9.

FIG. 11 shows another cross-sectional view of the cap shown in FIG. 9

FIG. 12 shows an end view of the cap shown in FIG. 9.

FIG. 13 shows another end view of the cap shown in FIG. 9.

FIG. 14 shows another end view of the cap shown in FIG. 9.

FIG. 15 shows a top view of a nozzle portion according to the present invention.

FIG. 16 shows a side view of the nozzle portion shown in FIG. 15.

FIG. 17 shows an end view of the nozzle portion shown in FIG. 15.

FIG. 18 shows an end view of the nozzle portion shown in FIG. 15.

FIG. 19 shows a partial cross-sectional side view of the nozzle portion shown in FIG. 15.

FIG. 20 shows an end view of the nozzle portion shown in FIG. 15.

FIG. 21 shows an end view of the nozzle portion shown in FIG. 15.

FIG. 22 shows a side view of a plunger according to the present invention.

FIG. 23 shows another side view of the plunger shown in FIG. 22.

FIG. 24 shows a partial view of the plunger shown in FIG. 22.

FIG. 25 shows a partial cross-sectional view of the plunger shown in FIG. 22.

FIG. 26 shows an end view of the plunger shown in FIG. 22.

FIG. 27 shows a partial cross-sectional view of the plunger shown in FIG. 22.

FIG. 28 shows a partial view of the plunger shown in FIG. 22.

FIG. 29 shows a partial cross-sectional view of the plunger shown in FIG. 22.

FIG. 30 shows a partial cross-sectional view of the plunger shown in FIG. 22.

DETAILED DESCRIPTION OF PREFERRED EMBODIMENTS

FIGS. 1–1A show a preferred embodiment of a deformable lens injecting apparatus 14 for inserting a deformable intraocular lens through a small incision into an eye. Apparatus 14 includes generally, a lens injecting body 16 including a lens receiver 18, a nozzle portion 22 connected to the lens receiver 18 and a plunger slidably disposed relative to a lens delivery passageway 26 defined by the nozzle portion 22 and lens receiver 18.

The lens injecting body 16 of apparatus 14 shown in FIG. 1 is preferably an elongated hollow translucent member made of polyethylene having a proximal end 32 and a distal end 34 as shown in FIG. 2. The transverse cross-sectional profile of lens injecting body 16 includes a major axis 46 and a minor axis 48 as shown in FIG. 3. The exterior surface of lens injecting body 16 defines a proximal finger rest portion 36 as shown in FIGS. 2–4, and a distal tapering portion 38 which transitions to a proximal endplate 42. Endplate 42 includes a pair of outwardly extending tabs 44. Finger rest portion 36, distal tapering portion 38, endplate 42 and extending tabs 44 each define longitudinal axes which are parallel with the major axis 46 of the transverse cross-sectional profile of lens injecting body 16.

As shown in FIGS. 2–5, the interior surface of lens injecting body 16 defines a proximal entrance port 52 and a distal tapering portion 54 which transitions into a lens delivery passageway 56 having an exit 58 on the distal face of endplate 34.

Lens receiver 18 is attached to the distal face of endplate 34 as shown in FIGS. 2, 3 and 5. In the preferred embodiment shown, lens receiver 18 and lens injecting body 16 are manufactured as a one-piece assembly.

Lens receiver 18 includes a first portion defining a base portion 62 and second and third portions which define a first extension portion 64 and a second extension portion 66, respectively, as shown in FIG. 2. A first live hinge 72 between base portion 62 and first extension portion 64 allows first extension portion 64 to rotate about a first longitudinal axis relative to base portion 62. A second live hinge 74 between base portion 62 and second extension portion 66 allows second extension portion 66 to rotate about a second longitudinal axis relative to base portion 62. Preferably, first live hinge 72 and second live hinge 74 are parallel and equidistant from a longitudinal axis of lens delivery passageway 26.

In FIG. 3, first extension portion 64 and second extension portion 66 are shown substantially coplanar with base portion 62 and lens receiver 18 is said to be in an open configuration. Note that lens receiver 18 defines a platform 68 when in an open configuration. First and second extension portions, 64 and 66, respectively may be operated, i.e. rotated, to what is said to be a closed configuration, as shown in FIG. 3A. When lens receiver 18 is in a closed configuration the interior surfaces of base portion 62, first extension portion 64 and second extension portion 66, define a portion of lens delivery passageway 26. Preferably, first and second extension portions cooperate to snap lock together when lens receiver 18 is in a closed configuration.

Platform 68 of apparatus 14 is preferably configured to receive a deformable intraocular lens (not shown) in a non-deformed condition. First extension portion 64 includes a first edge gripping portion 82 and second extension portion 66 includes a second edge gripping portion 84. First and second edge gripping portions 82 and 84, respectively, serve to maintain the lens in proper position within platform 68. Note from FIG. 8 that platform 68 defines a tray portion 76 for receiving an optic portion of a deformable intraocular lens and preventing the same from contacting the surface of platform 68 during storage of an intraocular lens therein.

Apparatus 14 is preferably provided with a pre-loaded lens within lens receiver 18. As shown in FIGS. 9–14, a cap 86 is preferably provided with apparatus 14 for placement over lens receiver 18. Cap 86 is preferably configured to releasably engage lens receiver while in an open configuration, in other words, cap 86 is preferably configured to releasably engage platform 68. Cap 86 is further preferably configured to releasably engage platform 68 with a pre-loaded deformable intraocular lens provided therein in a non-deformed condition. As shown in FIGS. 10–14, the inner surface 86 of cap 86 includes a first extension portion contour 88, a base portion contour 92, and a second extension contour 94. Cap 86 is further provided with a tab 96 which frictionally contacts a surface on the distal portion of base portion 62 of lens receiver 18 to releasably engage cap 86 to lens receiver 18.

FIGS. 1 and 17–21 show nozzle portion 22 according to the present invention. Nozzle portion 22 includes a lens receiver contour portion 102 which is configured to engage lens receiver 18 when lens receiver 18 is in a closed configuration. Note that nozzle portion 22 thereby functions to ensure that lens receiver 18 is maintained in a closed configuration when nozzle portion 22 is mounted thereto. Nozzle portion includes a pair of holes 104 which engage tabs 44 of lens receiver 18 to lock nozzle portion 22 to lens receiver 18. As shown in FIGS. 8 and 17, base portion 62 of lens receiver 18 includes a web portion 96 which is engaged by a web contoured portion 98 of nozzle portion 22. Web portion 96 and web contoured portion 98 cooperate to guide the advancement of nozzle portion 22 onto lens receiver and to prevent relative rotation therebetween.

Nozzle portion 22 further includes an extending portion 106 which defines a portion of lens delivery passageway 26. Note that the portion of lens delivery passageway 26 within extending portion 106 of nozzle portion 22 communicates with that of lens receiver 18. Further note that lens delivery passageway tapers distally within nozzle portion extending portion 106 as shown in FIGS. 15, 16, 18, and 19.

Extending portion 106 of nozzle portion 22 further indicates a nozzle tip portion 108 having a first tip portion 112 and a second tip portion 114 as shown in FIGS. 15,16, 19, 20 and 21. First tip portion 112 and second tip portion 114 are separated by opposing channels 116. Note that second tip portion 114 extends distally beyond first tip portion 112.

FIGS. 22–29 show a plunger 28 according to the present invention. Plunger 28 includes a main portion 118 having a transverse cross-sectional profile which defines a web section having sections coincident as shown in FIG. 29. The proximal end of plunger 28 includes a finger rest portion 122. Main portion 118 transitions into a mid portion 124 including a first flare portion 126, a collar portion 128 and a second flare portion 132 as shown in FIGS. 22,25 and 28. Mid portion 124, in turn, transitions into plunger extending portion 134 which is configured for axial movement relative to lens delivery passageway 26. Extending portion 134 of plunger 28 includes a plunger tip portion 136 including a first tip portion 138 and a second tip portion 142 which define a tool, specifically, a lens control portion 144 therebetween. Note that first tip portion 138 defines a broader inner face than second tip portion 142, as shown in FIG. 28.

The preferred embodiment of apparatus 14 is preferably provided to a user partially assembled. Specifically, plunger 28 is preferably inserted within lens injecting body as shown in FIGS. 1 and 1A. Note that plunger 28 is preferably provided to the user with a removable retainer clip 146 attached to main portion 118 for preventing axial movement of plunger 28 relative to lens delivery passageway 26. Further, lens receiver 18 is preferably provided with a pre-loaded deformable intraocular lens within platform 76. Cap 86 is preferably attached to lens receiver 18 to protect lens receiver 18 and the deformable intraocular lens contained therein. To use apparatus 14, the user first removes cap 86.

Apparatus 14 of the present invention stores, deforms, and delivers a deformable intraocular lens to an eye. To use apparatus 14, a user first removes cap 86. Then, while grasping lens injecting body 16 in one hand, the user uses the thumb and forefinger of the free hand to operate lens receiver 18 from an open configuration to a closed configuration. During operation of lens receiver from an open configuration to a closed configuration the deformable intraocular lens contained therein is deformed, in other words, a cross-sectional profile of the lens is altered to enable the lens to be moved through the lens delivery passageway. Once the lens receiver 18 is in a closed configuration, nozzle portion 22 is connected to lens receiver 18 thereby creating a continuous lens delivery passageway 26 through lens receiver 18 and nozzle portion 22.

The retaining clip 146 is then removed from plunger 28 which allows plunger 28 to move axially relative to lens delivery passageway 26. The plunger is then advanced until plunger tip portion 136 engages the deformed intraocular lens within lens receiver 18. The lens control portion of the plunger tip is specifically configured to prevent damage to the lens during the lens delivery process.

Further advancement of the plunger causes the lens therein to be further deformed, i.e. compressed, and moved into that portion of lens delivery passageway within nozzle portion 22. Note that the ridges 78 shown in FIG. 6 minimize surface to surface contact between the deformed lens and the lens delivery passageway within lens receiver 18.

As the lens is moved out of nozzle tip portion 108, the forces set up as a consequence of the deformation of the lens are at least partially released while the lens is within the lens delivery passageway since first tip portion and second tip portion of the nozzle tip are configured to expand slightly outwardly. Further, since first tip portion extends distally beyond second tip portion ,the lens is biased downwardly as it exits from the lens delivery passageway. Once within the eye, the lens further returns from a non-deformed state and the specially configured plunger tip portion may be used to manipulate the lens into proper implanted position.

What is claimed is:

1. A deformable intraocular lens injecting apparatus for inserting a deformable intraocular lens through a small incision into an eye, said apparatus comprising:

a lens injecting body including a lens receiver connected to and extending from one end of said lens injecting body, said lens receiver configured to be operated between an open configuration for loading the deformable intraocular lens and closed configuration for folding the loaded deformable intraocular lens;

a nozzle portion provided with a tip portion configured to be inserted through a small incision into an eye, said nozzle portion configured for connection to said lens injecting body to assemble said lens injecting apparatus, said nozzle portion being provided with a nozzle portion receiver configured for receiving and accommodating substantially said entire lens receiver when in the closed configuration, said nozzle portion and said lens receiver defining a lens delivery passageway; and, a plunger slidably disposed within said lens injecting body and configured to engage a deformable intraocular lens within said lens delivery passageway and force said deformable intraocular lens through and out of said lens delivery passageway into said eye.

2. The apparatus according to claim 1, wherein said lens receiver of said lens injecting body is configured to alter a cross-sectional profile of a deformable intraocular lens loaded in said lens receiver when said lens receiver is operated from an open configuration to a closed configuration.

3. The apparatus according to claim 2, wherein said lens receiver defines a platform.

4. The apparatus according to claim 3, wherein said platform is configured to support edges of said deformable intraocular lens while maintaining substantially no contact with an optic portion of said deformable intraocular lens.

5. The apparatus according to claim 4, wherein said platform is provided with a lower tray portion positioned below said edge gripping portions of said platform, said tray portion being shaped so as to substantially make no contact with an optic portion of the deformable intraocular lens.

6. The apparatus according to claim 5, wherein said tray portion is provided with a scalloped surface to reduce friction between said deformable intraocular lens and said lens receiver when said lens receiver is in said closed configuration.

7. The apparatus according to claim 3, wherein said platform includes two substantially parallel hinges set apart a predetermined distance.

8. The apparatus according to claim 7, wherein said hinges are live hinges.

9. The apparatus according to claim 7, wherein said platform is provided with edge gripping portions configured for gripping edges of a deformable intraocular lens to facilitate manipulation of said deformable intraocular lens when said lens receiver is operated from an open configuration to a closed configuration.

10. The apparatus according to claim 9, wherein said lens receiver is configured to be operated by the thumb and forefinger of a user pressing on edges of said lens receiver.

11. The apparatus according to claim 1, wherein said lens receiver of said lens injecting body is configured to compress a deformable intraocular lens loaded in said lens receiver when said lens receiver is operated from an open configuration to a closed configuration.

12. The apparatus according to claim 1, wherein said lens receiver of said lens injecting body is configured to compress a deformable intraocular lens loaded in said lens receiver when said lens receiver is operated from an open configuration to a closed configuration.

13. An apparatus according to claim 1, wherein said lens receiver is configured to support a deformable intraocular lens in a non-deformed condition when said lens receiver is in an open configuration.

14. The apparatus according to claim 1, including a pre-loaded deformable intraocular lens, said lens receiver being provided in an open configuration and configured to accommodate said pre-loaded deformable intraocular lens.

15. The apparatus according to claim 1, wherein said lens receiver is provided with a cap configured to engage said lens receiver when said lens receiver is in an open configuration.

16. The apparatus according to claim 15, including a pre-loaded intraocular lens said cap being further configured to engage said lens receiver when said lens receiver is provided with said pre-loaded deformable intraocular lens.

17. The apparatus according to claim 1, wherein said lens receiver includes a first portion and at least a second portion and operation of said lens receiver from an open configuration to a closed configuration is defined by relative movement between said first portion and said at least said second portion.

18. The apparatus according to claim 17, wherein said first portion and said at least said second portion are separate pieces of said lens receiver.

19. The apparatus according to claim 18, wherein said first portion is a base portion and said at least said second portion is an extension portion connected to said first portion by a live hinge and operation of said lens receiver from an open configuration to a closed configuration is defined by relative hinged movement between said first portion and said second portion.

20. The apparatus according to claim 19, wherein a third portion is an extension portion connected to said first portion by a live hinge and operation of said lens receiver from an open configuration to a closed configuration is further defined by relative hinged movement between said first portion and said third portion.

21. The apparatus according to claim 17, wherein operation of said lens receiver from an open configuration to a closed configuration includes relative sliding movement between said first portion and said second portion.

22. The apparatus according to claim 17, wherein connection of said nozzle portion to said lens receiver causes said lens receiver to be operated from an open configuration to a closed configuration.

23. The apparatus according to claim 1, wherein said lens receiver is configured to lock into said closed configuration when operated from said open configuration to said closed configuration.

24. The apparatus according to claim 1, wherein said lens injecting body and said lens receiver define a one-piece assembly.

25. The apparatus according to claim 1, wherein said lens injecting body and said lens receiver are separate pieces.

26. The apparatus according to claim 1, wherein said lens receiver is a cartridge configured to connect to said lens injector body.

27. The apparatus according to claim 1, wherein a removable retaining clip is provided to prevent relative movement between said plunger and said lens delivery passageway.

28. The apparatus according to claim 1, wherein said nozzle tip portion defines a lens manipulation tool.

29. The apparatus according to claim 1, wherein said nozzle tip portion defines a release portion for releasing an elastic force set up in said lens.

30. The apparatus according to claim 1, wherein said plunger includes a plunger tip portion defining a lens contour portion for facilitating engagement of said deformable intraocular lens.

* * * * *